(12) United States Patent
Hart et al.

(10) Patent No.: US 9,177,769 B2
(45) Date of Patent: Nov. 3, 2015

(54) INTERDIGITATED ELECTRODE CONFIGURATION FOR ION FILTER

(75) Inventors: Matthew Hart, London (GB); Andrew Koehl, Cambridge (GB)

(73) Assignee: Owlstone Limited, Cambridge (GB)

( * ) Notice: Subject to any disclaimer, the term of this patent is extended or adjusted under 35 U.S.C. 154(b) by 1777 days.

(21) Appl. No.: 12/442,921

(22) PCT Filed: Sep. 25, 2007

(86) PCT No.: PCT/GB2007/050581
§ 371 (c)(1),
(2), (4) Date: Jan. 29, 2010

(87) PCT Pub. No.: WO2008/038046
PCT Pub. Date: Apr. 3, 2008

(65) Prior Publication Data
US 2010/0148051 A1    Jun. 17, 2010

(30) Foreign Application Priority Data

Sep. 26, 2006  (GB) .................................. 0618926.0

(51) Int. Cl.
*H01J 49/00* (2006.01)
*H01J 49/06* (2006.01)
*G01N 27/62* (2006.01)
*H01J 49/42* (2006.01)

(52) U.S. Cl.
CPC ............ *H01J 49/061* (2013.01); *G01N 27/622* (2013.01); *H01J 49/0018* (2013.01); *H01J 49/421* (2013.01)

(58) Field of Classification Search
USPC .......... 250/281, 282, 287, 290, 291, 293, 294
See application file for complete search history.

(56) References Cited

U.S. PATENT DOCUMENTS

| | | | |
|---|---|---|---|
| 5,789,745 A | 8/1998 | Martin et al. | |
| 6,326,615 B1 * | 12/2001 | Syage et al. | 250/287 |
| 6,479,815 B1 * | 11/2002 | Goebel et al. | 250/287 |
| 6,806,466 B2 * | 10/2004 | Guevremont et al. | 250/287 |

(Continued)

FOREIGN PATENT DOCUMENTS

| | | |
|---|---|---|
| GB | 0521451 A | 5/1940 |
| GB | 2391694 A | 2/2004 |

(Continued)

OTHER PUBLICATIONS

L.A. Buryakov et al., Int. J. Mass. Spectrom. Ion Process. 128 (1993) 143.

(Continued)

*Primary Examiner* — Jack Berman
*Assistant Examiner* — Jason McCormack
(74) *Attorney, Agent, or Firm* — Locke Lord LLP; Barry Kramer; Christopher J. Capelli

(57) ABSTRACT

An ion filter (10) for use in ion mobility spectrometry is described, together with a method for manufacturing the filter. The filter (10) is manufactured by removing portions from a monolithic structure to form a pair of electrodes which remain mechanically connected. The connecting portion (22) provides sufficient electrical impedance between the electrodes to effectively electrically separate the electrodes. The connecting portion may be doped or chemically modified to obtain a desired impedance, or this may be obtained through appropriate selection of physical dimensions.

23 Claims, 2 Drawing Sheets

(56) References Cited

U.S. PATENT DOCUMENTS

| | | |
|---|---|---|
| 7,468,570 B2 * | 12/2008 | Ionel et al. ............. 310/216.009 |
| 2001/0042826 A1 | 11/2001 | Chutjian et al. |
| 2002/0106681 A1 * | 8/2002 | Wexler et al. ...................... 435/6 |
| 2005/0167584 A1 * | 8/2005 | Kernan et al. ................. 250/290 |
| 2005/0218320 A1 * | 10/2005 | Guevremont et al. ........ 250/292 |
| 2006/0231751 A1 * | 10/2006 | Zuleta et al. .................. 250/287 |
| 2007/0040113 A1 * | 2/2007 | Monroe et al. ................ 250/290 |
| 2007/0051956 A1 * | 3/2007 | Shih et al. ........................ 257/69 |
| 2008/0054174 A1 * | 3/2008 | Boyle et al. ................... 250/286 |
| 2008/0191132 A1 * | 8/2008 | Boyle et al. ................... 250/287 |
| 2009/0189064 A1 * | 7/2009 | Miller et al. .................. 250/282 |
| 2011/0036973 A1 * | 2/2011 | Alonso et al. ................. 250/282 |

FOREIGN PATENT DOCUMENTS

| | | |
|---|---|---|
| WO | WO-2006013396 A2 | 2/2006 |
| WO | WO-2006046077 A1 | 5/2006 |

OTHER PUBLICATIONS

E.V. Krylov et al., Int. J. Mass. Spectrom. On Process. 225 (2003) 39-51.

\* cited by examiner

22

INTERDIGITATED ELECTRODE CONFIGURATION FOR ION FILTER

FIELD OF THE INVENTION

The present invention relates to an ion filter comprising a particular electrode structure, and to a method of manufacturing such an ion filter. The filter is particularly suitable for use in ion mobility spectrometry, and in an ion pump.

BACKGROUND TO THE INVENTION

Ion mobility spectrometry is a versatile technique used to detect presence of molecular species in a gas sample. The technique has particular application in detection of explosives, drugs, and chemical agents in a sample, although it is not limited to these applications. Portable detectors are commonly used for security screening, and in the defence industry.

Ion mobility spectrometry relies on the differential movement of different ion species through an electric field to a detector; by appropriate selection of the parameters of the electric field, ions having differing properties will reach the detector at differing times, if at all. Time of flight (TOF) ion mobility spectrometry measures the time taken by ions when subject to an electric field to travel along a drift tube to a detector against a drift gas flow. By varying the electric field ions of different characteristics will reach the detector at different times, and the composition of a sample can be analysed. This form of spectrometry relies on the length of the drift tube for its resolution; the longer the drift tube, the more powerful the detector.

A variation on TOF ion mobility spectrometry is described in U.S. Pat. No. 5,789,745, which makes use of a moving electrical potential to move ions against a drift gas flow towards a detector. A plurality of spaced electrodes are alternately pulsed to generate a moving potential well, which carries selected ions along with it.

Field asymmetric ion mobility spectrometry (FAIMS) is a derivative of time of flight ion mobility spectrometry (TOFIMS), which potentially offers a smaller form factor; however, existing designs use moving gas flows and high voltages, which are undesirable for microchip implementations. Scaling is further hindered by molecular diffusion, an effect that becomes significant in the micron regime. Background information relating to FAIMs can be found in L. A. Buryakov et al. Int. J. Mass. Spectrom. Ion Process. 128 (1993) 143; and E. V. Krylov et al. Int. J. Mass. Spectrom. Ion Process. 225 (2003) 39-51; hereby incorporated by reference.

A further modification of FAIMS is described in international patent publications WO2006/013396 and WO2006/046077, the contents of which are incorporated herein by reference. The devices described in these publications make use of an electric field to cause ions to move toward the detector, and an ion filter comprising paired interdigitated electrode structures defining a plurality of ion channels through which ions may selectively pass, depending on the electric field applied between the electrodes. The paired electrodes must be electrically separated from one another; this is achieved by mechanical separation of the electrodes by forming them on an insulating substrate. To manufacture these electrodes, they must either be separately manufactured and then bonded onto a substrate, or they must be formed directly on the substrate.

As described in WO2006/013396, the electrodes may be manufactured using largely conventional microfabrication techniques. A conductive material is deposited on the top and bottom faces of a high resistivity silicon wafer substrate, followed by a photo resistant coating on each face. The top face is masked and subjected to photolithography, after which the coating of the top face is wet etched to provide an array of electrodes. The photoresist is stripped from both faces, and the process repeated to form the bottom face electrodes. A further resist coating is applied to the top face, after which the silicon is etched from the lower face using deep reactive ion etching to form channels. The photoresist is stripped for the final time, and the filter is ready for further processing.

In a variation of this technique, the silicon wafer may be initially bonded on the bottom face to a glass substrate; the various etching steps are then carried out from the top face to create channels and electrodes, after which the glass substrate is acid etched to expose the bottom face of the wafer, leaving a glass support in contact with the wafer.

The ion filter structure so produced may then be used in an ion mobility spectrometer device; or may be used in an ion pump, as described in GB 0521451.5.

A monolithic quadrupole mass spectrometer is described in GB 2 391 694, while US 2001/0042826 describes an ion filter including a two-dimensional array of poles forming one or more quadrupoles.

It would be advantageous to provide an alternative means of manufacturing an ion filter. In particular, it would be advantageous to reduce or remove the need for an insulative substrate.

SUMMARY OF THE INVENTION

According to a first aspect of the present invention, there is provided a method of manufacturing an ion filter, the method comprising providing a monolithic structure; selectively removing regions of the structure, to form a pair of electrodes defining at least one ion channel therebetween; the electrodes further being mechanically connected at one or more locations by a portion of the structure; wherein the connecting portion of the structure provides a higher electrical impedance than the filter would provide without such a mechanical connection, to thereby electrically separate the electrodes.

Preferably the monolithic structure comprises a wafer material, for example a silicon wafer. By 'monolithic', we mean that the structure is a single material, and is not made from a composite of separate materials.

This manufacturing process allows the paired electrodes of the ion filter to be produced from a single wafer, without the need to either deposit conductive regions on a substrate, or to form the electrodes separately and then secure them to a substrate. In addition, where the prior art makes use of a substrate, this substrate must also be etched to form suitable ion channels; this additional etching step is not necessary for the present invention.

Preferably the higher impedance of the connecting portion is obtained over the frequency range at which the filter is intended to operate; such higher impedances may also be obtained outside this range, but this is not essential.

Preferably the electrodes are interdigitated electrodes, each having at least one elongate finger.

The method may further comprise treating the connecting portion to alter its electrical impedance; preferably the treatment increases electrical impedance. Alternatively, or in addition, the method may comprise treating the electrodes to alter their electrical impedance; preferably the impedance is decreased. The precise treatment to be used will depend on the nature of the materials from which the filter is made, the desired alteration, and the desired level of impedance after treatment. For example, the structure may be doped, for example with boron, antimony, arsenic, or phosphorous. Suitable materials for the structure include silicon, which is most preferred, as well as germanium or gallium arsenide. The skilled person will be aware of other suitable materials for the structure and suitable dopants. Alternatively, the structure may be put under stress to alter its electrical impedance. A further approach is to locally chemically or otherwise modify the structure; for example, a silicon wafer may be oxidised to form silicon oxide which will alter the impedance of that portion of the wafer. Silicon nitride may also be used.

The connecting portion or the electrodes may be treated to alter impedance either before or after selective removal of regions of the structure. Preferably treatment takes place before selective removal of regions of the structure.

As an alternative to treating the electrodes or connecting portion to alter impedance, or in addition to such treatment, the method may comprise selecting one or more predetermined physical dimensions of the connecting portion and/or the electrodes to obtain a desired electrical impedance. In particular, the cross-sectional area of the connecting portion and/or the electrodes may be so selected; or the length to cross-sectional area ratio may be so selected. Other physical dimensions are suitable for such selection; the skilled person will be aware of how these may be selected to give a desired impedance.

Preferably the electrodes define one or more elongate fingers and an edge region, and the connecting portion is located in the edge region. Alternatively, or in addition, the connecting portion may be located on the elongate fingers; this may be at the tip or along the length of the fingers, provided there is sufficient unconnected space to define suitable ion channels.

A plurality of connecting portions may be present.

Preferably the electrodes each comprise a plurality of elongate fingers, defining between them a plurality of ion channels. The fingers may in certain embodiments be curved or serpentine, thereby defining similarly curved or serpentine ion channels.

Preferably a plurality of ion channels are present; preferably at least 5, at least 10, at least 15, or at least 20 ion channels.

The method may further comprise bonding the monolithic structure to a substrate.

According to a further aspect of the present invention, there is provided an ion filter comprising a monolithic structure defining a pair of electrodes defining at least one ion channel therebetween; the electrodes further being mechanically connected at one or more locations by a portion of the monolithic structure; wherein the connecting portion provides a higher electrical impedance than the filter would provide without such a mechanical connection, to thereby electrically separate the electrodes.

The monolithic structure is preferably a wafer, for example a silicon wafer.

The connecting portion may be treated, for example it may be doped or chemically altered, to alter its electrical impedance. Alternatively, or in addition, the electrodes may be so treated.

Alternatively, or in addition, the connecting portion and/or the electrodes may have one or more predetermined physical dimensions selected to obtain a desired electrical impedance. In particular, the cross-sectional area of the connecting portion and/or the electrodes may be so selected; or the length to cross-sectional area ratio may be so selected. Other physical dimensions are suitable for such selection; the skilled person will be aware of how these may be selected to give a desired impedance.

Preferably the electrodes define one or more elongate fingers and an edge region, and the connecting portion is located in the edge region. Alternatively, or in addition, the connecting portion may be located on the elongate fingers; this may be at the tip or along the length of the fingers, provided there is sufficient unconnected space to define suitable ion channels.

A plurality of connecting portions may be present.

Preferably the electrodes each comprise a plurality of elongate fingers, defining between them a plurality of ion channels. The fingers may in certain embodiments be curved or serpentine, thereby defining similarly curved or serpentine ion channels.

Preferably a plurality of ion channels are present; preferably at least 5, at least 10, at least 15, or at least 20 ion channels.

The ion filter may further comprise a substrate on which the structure is bonded.

A further aspect of the present invention provides an ion mobility spectrometer comprising an ioniser, an ion filter as herein described, and an ion detector. The spectrometer may further comprise means for driving ions through the ion filter; for example, a gas flow generator, and/or paired electrodes for generating a drive electric field through the filter. Other features of the spectrometer may be as described in WO2006/013396 and WO2006/046077, the contents of which are incorporated herein by reference.

A still further aspect of the present invention provides an ion pump incorporating an ion filter as herein described. There is provided a device for selectively transferring ionised species from a first space to a second space, the device comprising first and second spaces separated by an ion filter allowing selective communication between the spaces; the ion filter being as herein described. Other features of the device may be as disclosed in GB 0521451.5.

BRIEF DESCRIPTION OF THE DRAWINGS

These and other aspects of the present invention will now be described by way of example with reference to the accompanying drawings, in which.

DETAILED DESCRIPTION OF THE DRAWINGS

Figure 1:
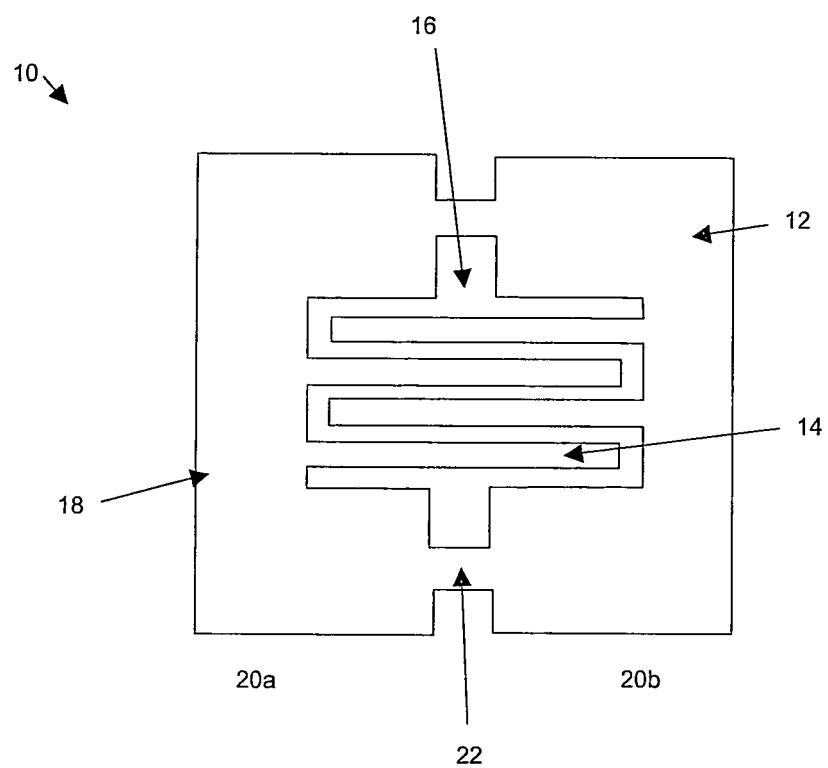
FIG. 1 shows a first embodiment of an ion filter according to an aspect of the present invention.

Referring to the Figures, these show first and second embodiments of an ion filter according to the present invention. The filter 10 is formed of a doped silicon wafer 12 which is initially solid. The wafer is typically around 0.3 mm in thickness. The wafer 12 is etched by means of deep reactive ion etching or other chemical or physical etching techniques in order to form a number of elongate fingers 14. The fingers between them define a number of ion channels 16 extending through the depth of the wafer. An outer edge 18 is left surrounding the fingers and channels. The elongate electrode fingers 14 and part of the edge 18 together define two distinct portions of the filter 10. The two portions 20a, 20b are connected mechanically by bridges 22 between the two portions formed in the edge 18.

The bridges 22 are formed so as to have a greater electrical impedance than the remainder of the ion filter, and in particular the electrode fingers 14. In a first embodiment, shown in FIG. 1, the dimensions of the bridges are chosen to provide a suitable impedance. For example, two bridges each with dimensions 1 mm long, 1 mm wide and 0.3 mm thick, made from a material with resistivity 2000 Ohm cm would have a combined parallel resistance just over 30 k Ohms.

Figure 2:
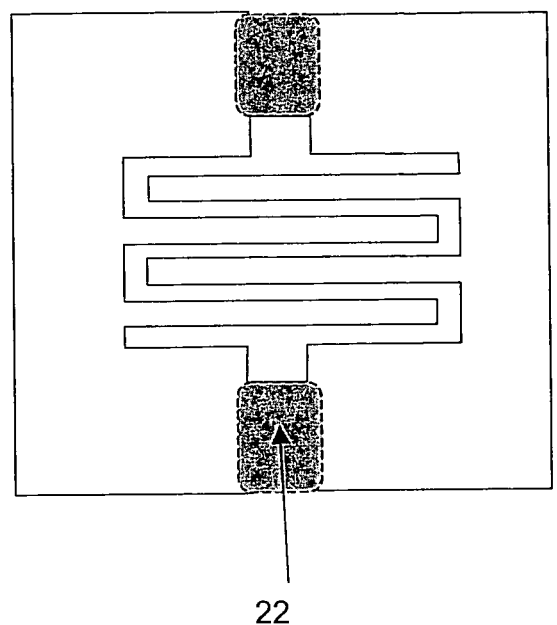
FIG. 2 shows a second embodiment of an ion filter according to an aspect of the present invention.

Alternatively, the wafer material may be doped or otherwise modified, for example by oxidation, at the bridges 22; this is illustrated in FIG. 2.

Thus, the present invention incorporates a mechanical linkage between the two electrodes into the same wafer used to form the electrodes themselves, rather than using a separate substrate. This mechanical linkage must still provide electrical isolation between the two electrodes; this can be done by forming the device from a suitable material (e.g. doped silicon) and ensuring that the regions forming the mechanical linkages have a high enough ratio of length to effective cross-sectional area to achieve the required isolation resistance for the resistivity used, or by selectively doping or otherwise modifying the material to form mechanical linkages that also achieve electrical isolation. In certain embodiments, both of these methods may be used.

The invention claimed is:

1. A method of manufacturing an ion filter, the method comprising providing a monolithic structure; selectively removing regions of the structure to define separated first and second filter opposing portions and to form a pair of interdigitated electrodes defining at least one ion channel therebetween wherein a first electrode is mechanically connected to and extends from said first filter portion and said interdigitated second electrode is mechanically connected to and extends from said second filter portion such that the first and second interdigitated electrodes extend toward one another from respective opposing said first and second filter portions; wherein a connecting portion connects the first and second filter portions of the structure which connection portion provides a higher electrical impedance between the first and second interdigitated electrodes than the filter would provide without such a connection, to thereby electrically separate the electrodes.

2. The method of claim 1, further comprising treating the connecting portion to alter its electrical impedance.

3. The method of claim 2 wherein the treatment increases electrical impedance.

4. The method of claim 1, further comprising treating the electrodes to alter their electrical impedance.

5. The method of claim 2, wherein the treatment comprises doping.

6. The method of claim 2, wherein the treatment comprises locally chemically modifying the monolithic structure to alter impedance.

7. The method of claim 2 wherein treatment takes place before selective removal of regions of the structure.

8. The method of claim 1 comprising selecting one or more predetermined physical dimensions of the connecting portion and/or the electrodes to obtain a desired electrical impedance.

9. The method of claim 1 wherein the electrodes define one or more elongate fingers and an edge region, and the connecting portion is formed in the edge region.

10. The method of claim 1 wherein the electrodes define one or more elongate fingers and the connecting portion is formed on the elongate fingers.

11. The method of claim 1 further comprising bonding the monolithic structure to a substrate.

12. An ion filter comprising a monolithic structure defining separated first and second filter portions and a pair of interdigitated first and second electrodes wherein each interdigitated electrode has a planar surface portion defined by an edge surface having at least opposing first and second side surfaces, the monolithic structure further defining at least one ion channel between the first and second electrodes; the electrodes further being mechanically connected to the monolithic structure via only a first side portion of each first and second electrode wherein a connecting portion connects the first and second filter portions of the structure which connecting portion provides a higher electrical impedance between the first and second electrodes than the filter would provide without such a connection, to thereby electrically separate the electrodes.

13. The filter of claim 12 wherein the connecting portion and/or the electrodes are treated to alter their electrical impedance.

14. The filter of claim 12 wherein the connecting portion and/or the electrodes have one or more predetermined physical dimensions selected to obtain a desired electrical impedance.

15. The filter of claim 12 wherein the electrodes define one or more elongate fingers and an edge region, and the connecting portion is located in the edge region.

16. The filter of claim 12 wherein the electrodes define one or more elongate fingers and an edge region, and the connecting portion is located on the elongate fingers.

17. The filter of claim 12 wherein a plurality of connecting portions are present.

18. The filter of claim 12 wherein the electrodes each comprise a plurality of elongate fingers, defining between them a plurality of ion channels.

19. The filter of claim 18 wherein the fingers are curved or serpentine.

20. The filter of claim 12 wherein a plurality of ion channels are present.

21. The filter of claim 12 further comprising a substrate on which the monolithic structure is bonded.

22. An ion mobility spectrometer comprising an ioniser, an ion filter as described in claim 12, and an ion detector.

23. A device for selectively transferring ionised species from a first space to a second space, the device comprising first and second spaces separated by an ion filter allowing selective communication between the spaces; the ion filter being as described in claim 12.

* * * * *